United States Patent [19]

Rzasa

[11] 4,211,231
[45] Jul. 8, 1980

[54] CRYOSURGICAL INSTRUMENT

[75] Inventor: Ronald P. Rzasa, Fairfield, Conn.

[73] Assignee: Cryomedics, Inc., Bridgeport, Conn.

[21] Appl. No.: 906,213

[22] Filed: May 15, 1978

[51] Int. Cl.² .......................... A61B 17/36; A61F 7/12
[52] U.S. Cl. .................................... 128/303.1; 62/293
[58] Field of Search .................... 128/303.1, 400, 401, 128/399; 62/293, 514 JT

[56] References Cited

U.S. PATENT DOCUMENTS

| 3,439,680 | 4/1969 | Thomas, Jr. | 128/303.1 |
| 3,651,813 | 3/1972 | Bryne | 128/303.1 |
| 3,664,344 | 5/1972 | Bryne | 128/303.1 |
| 3,696,813 | 10/1972 | Wallach | 128/303.1 |
| 3,712,306 | 1/1973 | Bryne | 128/303.1 |
| 3,807,403 | 4/1974 | Stumpf et al. | 128/303.1 |
| 3,933,156 | 1/1976 | Riggi | 128/303.1 |
| 3,934,589 | 1/1976 | Zimmer | 128/303.1 |

Primary Examiner—Robert W. Michell
Assistant Examiner—Arthur S. Rose

Attorney, Agent, or Firm—Barry Kramer

[57] ABSTRACT

A cryosurgical instrument which may be used with interchangeable spray and closed end cryotips includes a body member with a central bore extending partially therethrough. Refrigerant is supplied to a first point in the bore through a valved refrigerant supply line while an effluent opening connects an effluent line to a second point in the bore. The bore receives the inner ends of cryotips. All cryotips used with the instrument include refrigerant delivery tubes having inner ends which are positioned adjacent the first point in the bore and O-rings which are seated between the first point and the second point in the bore to prevent escape of refrigerant. Closed end cryotips to be used with the instrument further include an effluent channel extending from an expansion chamber to the second point in the bore. A second O-ring is provided with closed end cryotips. The second O-ring is seated between the second point in the bore and its open end to prevent escape of effluent refrigerant flowing through the effluent channel.

5 Claims, 5 Drawing Figures

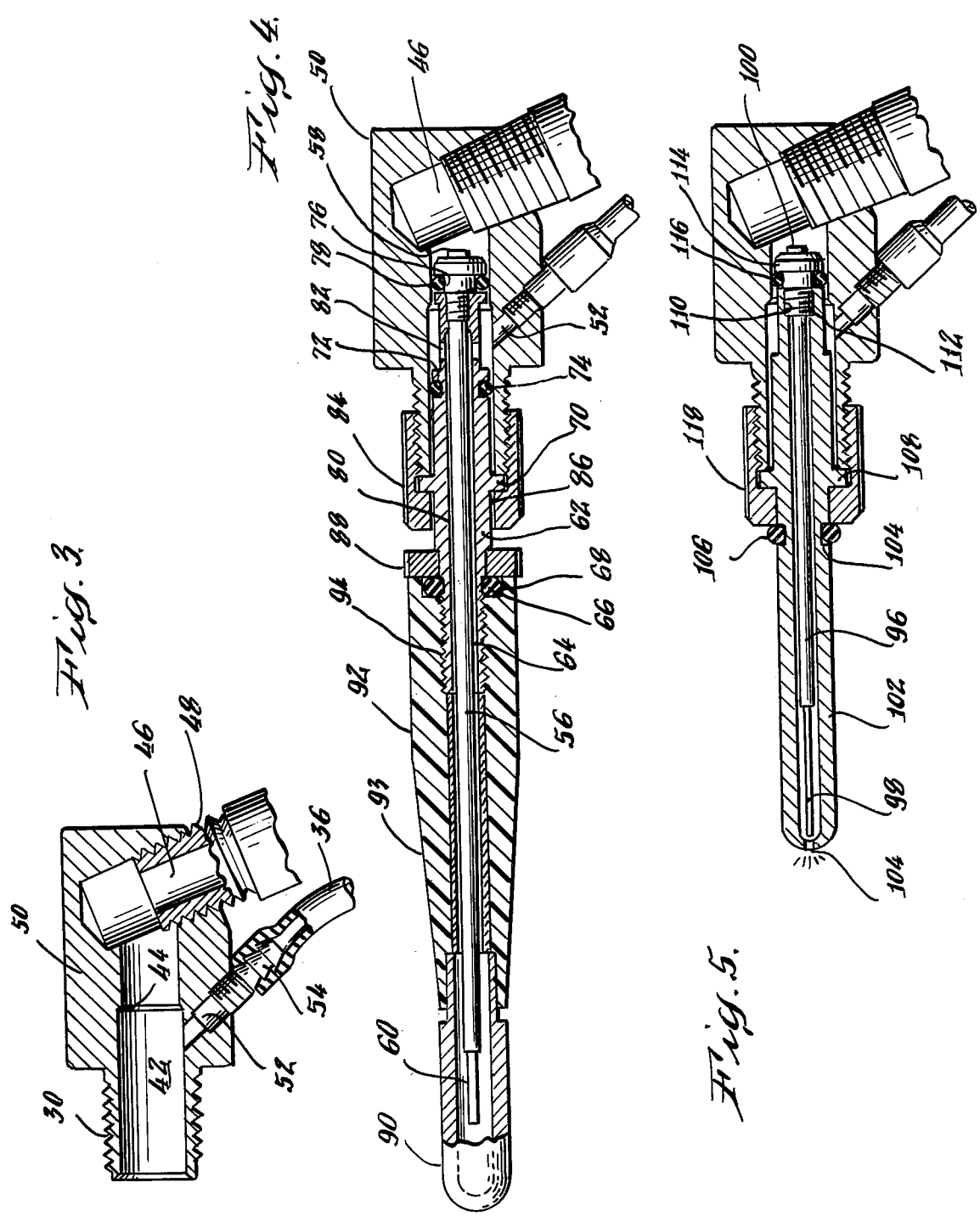

CRYOSURGICAL INSTRUMENT

BACKGROUND OF THE INVENTION

The present invention relates to cryosurgical instruments and more particularly to a cryosurgical instrument which may be used with a number of different, interchangeable spray and closed end cryotips.

Cryosurgery can be used in treating a number of different medical conditions. For example, cryosurgery can be used in the treatment of hemorrhoids, in removal of undesirable growths or skin tumors, in the course of ophthalmic operations and for many other similar and dissimilar surgical procedures. In some of these procedures, a spray cryotip is used to spray cold refrigerant liquid directly onto the tissue to be necrosed. Contact with the liquid and evaporation of the liquid from the tissue lowers the tissue temperature sufficiently to provide necrosis. In other procedures, a closed end cryotip is used. In such a cryotip, a refrigerant fluid, which may be either gas or liquid, is delivered to an expansion chamber within the cryotip. The cryotip is formed from a material having a high thermal conductivity. The expanding refrigerant cools the cryotip which is placed in direct contact with the tissue to be treated to bring about necrosis of that tissue.

The amount of tissue to be treated and the accessability of that tissue varies with the cryosurgical procedure to be performed. For that reason, special purpose cryotips have been developed for particular procedures.

Cryosurgical instruments have also been developed which may be used with interchangeable closed end cryotips. The cryotips used with such instruments have basically the same internal structure, differing from one another only in the external configuration.

However, because the construction of spray cryotips is dissimilar to the construction of closed end cryotips, those instruments which could accept interchangeable closed end cryotips could not accept spray cryotips.

Since the surgeon might need both types of cryotips in his practice, he either had to buy separate cryosurgical instruments for use with two different types of tips or avoid performing certain types of cryosurgical procedures.

U.S. Pat. No. 3,651,813 discloses a cryosurgical instrument in which a delivery tube is permanently connected to a container of liquified gas coolant. The container is attached directly to a handle having a channel which may be left open to relieve gas pressure in the container when the instrument is not in use. When the instrument is to be used, this channel is closed to allow gas pressure in the container to build up at ambient temperatures so as to force liquid coolant through a dip tube, actually an extension of the delivery tube. The instrument can be used either as a spray-type instrument or, by threading a cap onto the end of the delivery tube, as a closed end type instrument. When used in the closed end mode, effluent refrigerant is exhausted through an effluent channel terminating at the handle of the instrument.

Since the delivery tube is an integral part of the instrument, its dimensions cannot be changed to allow the instrument to perform different cryosurgical procedures as efficiently as a cryosurgical instrument having a tip with a delivery tube and an outer casing specifically designed for that procedure. Moreover, the effluent refrigerant is exhausted relatively near the tissue being treated. This is generally undesirable since the refrigerant is not always as sterile as might be desired. Finally, since the refrigerant pressure is relatively low, the refrigerant delivery rate may not be adequate for certain types of cryosurgical procedures.

SUMMARY OF THE INVENTION

The present invention is a cryosurgical instrument which can be used with a number of different and interchangeable spray and closed end tips.

The instrument includes a refrigerant supply line which may be connected to a source of refrigerant fluid. A valve is connected in the supply line for controlling the flow of refrigerant from the source. The instrument further includes an effluent line for conveying effluent refrigerant away from the vicinity of the instrument. A body member has a central bore open at one end, a refrigerant inlet opening providing a fluid flow path between one end of the refrigerant supply line and a first point within the central bore. The body member includes means for securing either spray or closed end cryotips in position. The cryotips which are used all have delivery tube assemblies with an inner end which is secured in a position adjacent the first point in the central bore. All of the cryotips further include a fluid sealing means for providing a fluid seal within the central bore between the first point and the second point. Closed-end cryotips used with the instrument include an exhaust channel which directs effluent refrigerant to the vicinity of the second point. Closed-end cryotips further include a fluid sealing means for providing a fluid seal between the second point and the open end of the bore.

DESCRIPTION OF THE DRAWINGS

While the specification concludes with claims particularly pointing out and distinctly claiming that which is regarded as the present invention, details of a preferred embodiment of the invention may be more readily ascertained from the following detailed description when read in conjunction with the accompanying drawings wherein:

FIG. 3 is a cross section of a body member used in the cryosurgical instrument;

FIG. 4 is a partial cross section of a closed end cryotip mounted in the body member of FIG. 3; and FIG. 5 is a partial cross section of a spray cryotip mounted in the body member of FIG. 3.

DETAILED DESCRIPTION

Figure 1:
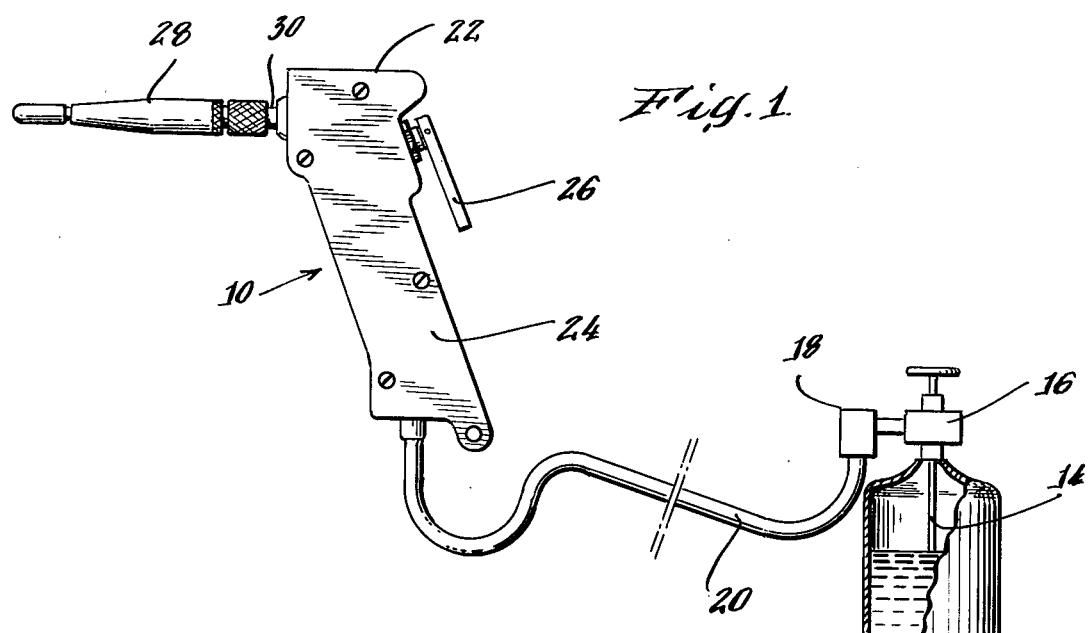
FIG. 1 is a partially schematic view of one embodiment of a cryosurgical instrument constructed in accordance with the present invention.

Referring to FIG. 1, a cryosurgical instrument 10 constructed in accordance with the present invention is supplied with refrigerant from a canister 12 containing a coolant such as N$_2$O at a pressure on the order of 600–800 psi. The canister 12 includes a dip tube or siphon tube 14 for carrying liquid coolant through a canister valve 16 and a connector unit 18 to a flexible hose 20 which, in a preferred embodiment, includes both a refrigerant supply line for carrying refrigerant to the instrument 10 and a separate effluent line for conducting effluent refrigerant from the instrument 10 to the connector unit 18. The effluent line ends at unit 18, allowing effluent refrigerant to enter the atmosphere through layers of acoustic packing material.

The instrument 10 includes a housing 22 which protects the internal components of the instrument while providing a gripping surface. In a preferred embodiment, the housing 22 includes a pistol grip 24 having a valve-actuating trigger 26 extending parallel to one surface of the pistol grip. A closed tip cryosurgical probe 28, which represents only one of the many different kinds of spray or closed end cryotips which may be used with instrument 10, is shown secured to the instrument at an externally-threaded stud 30 extending from one face of the instrument.

Figure 2:
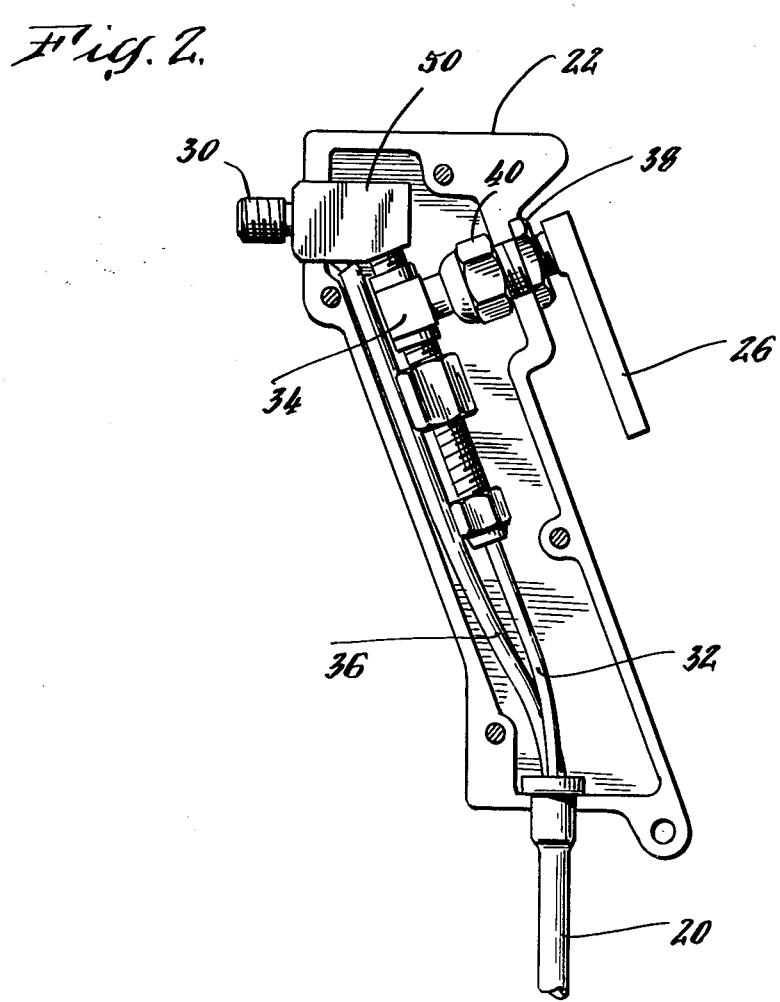
FIG. 2 is a side view of the instrument shown in FIG. 1 without a cryotip and with one half of the handle removed to disclose the internal components.

FIG. 2 is a view of the components which would normally be obscured from view by one half of the housing 22. The instrument includes a body member 50 which includes the threaded stud 30. Body member 50, which will be described in more detail later, is connected to the supply of refrigerant through a refrigerant supply line 32 which includes a conventional valve 34 for controlling the flow of refrigerant. Valve 34 is a normally closed valve which may be biased open by depressing trigger 26 to permit refrigerant to flow through line 32 and into body member 50. One suitable valve is a model no. OGM2 manufactured by Whitey Company, Inc. of Oakland, California.

The body member 50 is also connected to an effluent line 36 which can carry effluent refrigerant from the body member 50, through hose 20 to the connector unit 18. In a preferred embodiment, the illustrated components are not fastened to the housing 22 but are held in place between opposite halves of the housing. The valve 34 is held in a stationary position relative to the housing by means of a nut 38 which rests against the outer surface of the housing and a valve casing 40 which rests against the inner surface of the housing at the valve actuator stem.

Referring to FIG. 3, the body member 50 may be machined from a single block of metal with threads being cut on the external surface of the stud 30 at one end of the body. A central bore 42 extends part way through the body 50. The bore 42 is somewhat larger from its open end to a shoulder 44 than it is from shoulder 44 to the closed end. A refrigerant inlet opening 46 which is preferably internally threaded, connects the refrigerant supply line to a first point on the central bore. The refrigerant supply line is represented by threaded connector 48 which leads directly to the valve 34 discussed with reference to FIG. 2. An effluent opening 52 provides a fluid flow path between a second point within central bore 42 and an effluent line. A connector 54 may be threaded into the effluent opening 52. Connector 54 includes a serrated surface which permits the effluent line to be easily assembled while resisting any disassembly.

Two basically different types of cryotips are adapted to be secured to the instrument 10 at the body member 50. FIG. 4 illustrates a typical closed end cryotip. The cryotip includes a hollow delivery tube 56 having a porous filter 58 at its inner end and a flow restriction 60 such as a capillary tube at its outer end. The delivery tube 56 is carried by a hollow member 62 which includes an externally threaded segment 64 at one end, a groove 66 for receiving a fluid sealing element such as O-ring 68 at the base of the threaded segment 64, and a shoulder 70. The member 62 further includes a second circumferential groove 72 for receiving a fluid sealing means such as O-ring 74 and another circumferential groove 76 for retaining a third O-ring 78.

The delivery tube 56 extends through and is generally coaxial with the opening through the member 62. Delivery tube 56 is somewhat smaller than the opening through member 62, forming an annular exhaust channel 80 which extends from the end of the threaded segment 64 to openings 82 in member 62 providing a fluid flow path between the exhaust channel 80 and the central bore adjacent the effluent opening 52 through body 50.

The assembly described above is attached to the body member 50 by means of a cup shaped nut 84 having an internally threaded bore complementary to the externally threaded stud 30 on body 50. The nut 84 has a through hole 86 which is somewhat larger than the outer diameter of the member 62 allowing the nut to rotate freely on member 62. Lateral movement of the nut 84 is limited, however, by shoulder 70 on member 62 and by a knurled disc 88.

To secure the member 62 and the delivery tube 56 in place in body 50, the end of the delivery tube assembly is inserted as far as possible into the central bore 42. When the nut 84 comes into contact with the threaded stud 30, nut 84 is turned onto the threaded stud. As the nut 84 is drawn onto the threaded stud, it forces shoulder 70 (and member 62) to the right or further into central bore 42. When the member 62 is in position, the O-ring 78 prevents the escape of supplied refrigerant along the central bore. O-rings 78 and 74 limit effluent refrigerant to the vicinity of the central bore 42 adjacent the effluent opening 50.

A variety of different closed end cryotips can be used in combination with the above-described assembly. While the shape and size of the closed end cryotips will vary depending upon the particular cryosurgical procedure to be performed, all will have a body contacting member made of high thermal conductivity material such as coin silver. In the illustrated tip, the body contacting member is a cylinder 90 having a rounded end. The inner walls of the member 90 define an expansion chamber into which refrigerant supplied through flow restriction 60 is expanded to cool the member 90. The member 90 is brazed or otherwise secured to a thin-walled metal tube 93, preferably a stainless steel material. A hollow sleeve 92, made from a material having a relatively low thermal conductivity, is press-fitted onto or otherwise secured to tube 93. Sleeve 92 contains an internally threaded segment 94 with the threads being complementary to the externally threaded segment 64 of member 62 to permit the sleeve 92 to be threaded into position on member 62. The internal diameter of tube 93 is larger than the external diameter of the delivery tube 56. Effluent refrigerant flows through the annular space between the delivery tube 56 and the tube 93. O-ring 68 prevents the loss of effluent refrigerant at the interface between disc 88 and the inner end of the sleeve 92.

A typical spray type cryotip for use with the instrument described above is shown in FIG. 5. The spray-type cryotip includes a delivery tube 96 having a flow restriction 98 adjacent one end. Refrigerant is supplied to the hollow refrigerant delivery tube 96 is carried within a member 102 having a small opening 104 aligned with the end of the flow restriction 98. Member 102 includes a cylindrical recess 104 for receiving an O-ring 106, a protruding shoulder 108 and an internally threaded segment 110 adjacent its right end. The delivery tube 96 includes an externally threaded segment 112 and a flange 114. In assembling the spray cryotip, the delivery tube 96 is threaded into the member 102 with a fluid sealing O-ring 116 being trapped between the right end of member 102 and the flange 114 on the delivery tube assembly. The O-ring 116 prevents supplied refrigerant from escaping along the length of the central bore 42.

It will be noted that no exhaust channel is provided in the spray cryotip since the refrigerant is intended to leave the tip as a fine stream. The spray cryotip is secured to the body 50 in the same manner as the closed end cryotip; namely, by means of a cup-shaped nut 118 having internal threads complimentary to the external threads on the stud 30. The effluent line 36 remains connected to the central bore when spray cryotips are in place but serves no function.

The cryosurgical instrument described above is thought to have performance characteristics superior to those of prior art instruments. Since the entire cryotip is replaced and not just an end cap, the delivery tube assembly and outer housing of the cryotips can be optimized for the type of refrigerant and the type of cryosurgical procedure to be performed. Effluent refrigerant is conducted safely away from the cryosurgical instrument, entering the atmosphere only at the muffler 18 which is remote from the instrument. Moreover, the refrigerant is supplied at relatively high pressure to provide a high refrigerant delivery rate to either type of cryotip. When a spray cryotip is in place, the result is a fine stream of cold liquid refrigerant delivered at a high rate.

While there has been described what is considered to be a preferred embodiment of the invention, variations and modifications therein may occur to those skilled in the art once they become acquainted with the basic concepts of the invention. Therefore, it is intended that the appended claims shall be construed to include all such variations and modifications as fall within the true spirit and scope of the invention.

What is claimed is:

1. A cryosurgical instrument comprising:

means defining a body having opposing extremities and provided with an elongate bore therein extending through the surface of said body means to define a receiving opening in one extremity of said body means, said body means including a refrigerant fluid inlet passageway therein communicating with said bore at a first point spaced from said receiving opening and adjacent the opposite extremity of said body means, said refrigerant fluid inlet passageway being adapted to be coupled with a source of refrigerant fluid, said body means further including a refrigerant effluent outlet passageway therein communicating with said bore at a second point between said receiving opening and said first point;

a kit including first and second, unitary, integrated cryotip assemblies, said first cryotip assembly having a distal and a proximal end and comprising (1) an outer, elongate, hollow tube having a distal and a proximal end, the distal end thereof being closed to define a gas expansion chamber, said outer tube having an exhaust opening therein adjacent the proximal end thereof, and (2) an inner, elongate, hollow tube for supplying refrigerant to said expansion chamber, having a distal and a proximal end and being concentrically disposed within said outer tube such that the distal end of the inner tube opens into said expansion chamber and the proximal end of said inner tube is located adjacent the proximal end of said outer tube, said inner tube being radially spaced from the outer tube to define an annular exhaust channel between said inner and outer tubes communicating with said exhaust opening in said outer tube, said inner tube being secured to said outer tube and having both ends thereof essentially open, said second cryotip assembly having a distal and a proximal end and comprising (1) an outer, elongate, hollow tube having a distal and proximal end a refrigerant fluid delivery opening in the distal end thereof, the proximal end of said last named tube being closed, and (2) an inner, elongate, hollow tube for supplying refrigerant to said delivery opening, having a distal and a proximal end, said last named inner tube being disposed within said last named outer tube such that the distal end of the inner tube opens into said delivery opening and the proximal end of said inner tube is located adjacent the proximal end of said outer tube and having each end thereof essentially open, said last named inner tube being secured to said last named outer tube; the proximal end of each of said cryotip assemblies being sized such that each of said cryotip assemblies may be received within said bore, manipulable means for selectively securely either of said first and second cryotip assemblies on said body means, said manipulable securing means including a first portion carried by each said first and second cryotip assemblies, and a second portion carried by said body means adjacent said receiving opening, the proximal ends of each of said cryotip assemblies being such that when either of said cryotip assemblies is secured to said body means said proximal end of said inner tube extends to a position within said bore between said first and second points, first means for providing a fluid seal between said inner tube and said body means at an area in said bore between said first and second points such that when either of said cryotip assemblies is secured to said body means refrigerant fluid entering said bore from said inlet passage is directed into said proximal end of said inner tube, the outer tube of said first cryotip assembly being such that when said first cryotip assembly is secured to said body means and said outer tube of said first cryotip assembly extends to a position within said bore between said receiving opening and said first fluid seal means such that said exhaust opening in said outer tube of said first cryotip assembly is in fluid communication with said outlet passage, second means for providing a fluid seal between said outer tube of said first cryotip assembly and said body means at an area in said bore between said second point and said receiving opening such that refrigerant fluid exhausted through said exhaust opening is directed to said outlet passage, said first and second portions of said manipulable securing means being releasably engagable with each other for releasably securing the corresponding one of said first and second cryotip assemblies on said body means, with said open end of said outer tube of said first cryotip assembly extending into said bore through said receiving opening when said first cryotip assembly is secured to said body means, and with the closed end of said outer tube of said second cryotip assembly extending into said bore through said receiving opening when said second cryotip is secured to said body means, each of said first and second cryotip assemblies being removable as an integral unit from said body means by operation of said manipulable securing means to permit interchangeably securing either of said first and second cryotip assemblies to said body means.

2. An instrument as defined by claim 1, wherein said first and second portions of said manipulable securing means are defined by a threaded coupling.

3. An instrument as defined by claim 1, wherein said first portion of said manipulable securing means comprises a pair of threaded nuts respectively rotatably mounted on said first and second cryotip assemblies, and said second portion of said manipulable securing means comprises a series of threads on said body means circumscribing said elongate bore.

4. An instrument as defined by claim 3, wherein each of said first and second cryotip assemblies further includes an annular shoulder member on the periphery thereof and each of said nuts includes an annular groove therein for slidably confining the corresponding shoulder member therewithin.

5. The instrument as defined by claim 1, wherein said first cryotip assembly is generally circular in cross-section and includes a neck of reduced diameter which is interposed between said first and second points in said bore when first cryotip assembly is secured to said body means.

* * * * *